United States Patent
Hulliger

(10) Patent No.: US 9,975,679 B2
(45) Date of Patent: May 22, 2018

(54) MULTI PACKAGING SYSTEM FOR MEDICAL IMPLANTS

(75) Inventor: Urs Hulliger, Langendorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 756 days.

(21) Appl. No.: 13/185,205

(22) Filed: Jul. 18, 2011

(65) Prior Publication Data

US 2012/0181200 A1    Jul. 19, 2012

Related U.S. Application Data

(60) Provisional application No. 61/367,984, filed on Jul. 27, 2010.

(51) Int. Cl.
| | |
|---|---|
| B65D 75/52 | (2006.01) |
| A61B 50/22 | (2016.01) |
| A61B 90/96 | (2016.01) |
| A61B 50/20 | (2016.01) |
| A61B 17/86 | (2006.01) |
| A61B 50/30 | (2016.01) |
| A61B 90/00 | (2016.01) |

(52) U.S. Cl.
CPC ............ *B65D 75/527* (2013.01); *A61B 50/20* (2016.02); *A61B 50/22* (2016.02); *A61B 50/30* (2016.02); *A61B 90/96* (2016.02); *A61B 17/865* (2013.01); *A61B 2050/318* (2016.02); *A61B 2090/0807* (2016.02)

(58) Field of Classification Search
USPC ....... 206/339, 461, 591, 370, 363, 365, 332, 206/464, 806, 814, 207, 349, 485
See application file for complete search history.

(56) References Cited

U.S. PATENT DOCUMENTS

| | | | |
|---|---|---|---|
| 1,803,602 A * | 5/1931 | Dey | 206/459.5 |
| 3,288,280 A | 11/1966 | Bostrom | |
| 3,933,245 A | 1/1976 | Mullen | |
| 4,121,711 A | 10/1978 | Bolanowski | |
| 4,168,002 A * | 9/1979 | Crosby | 206/459.5 |
| 4,211,329 A * | 7/1980 | Braverman | 206/534 |
| 4,324,331 A * | 4/1982 | Ignasiak | 206/363 |
| 4,666,040 A * | 5/1987 | Murata | 206/441 |
| 4,757,898 A * | 7/1988 | Klein | 206/459.1 |
| 5,121,835 A * | 6/1992 | Grupe | 206/459.5 |
| 5,249,672 A | 10/1993 | Brown et al. | |
| 5,370,220 A * | 12/1994 | Wang | 206/738 |
| 5,386,912 A | 2/1995 | Holzwarth et al. | |
| 5,615,766 A * | 4/1997 | Gemma et al. | 206/63.3 |
| 5,620,087 A * | 4/1997 | Martin et al. | 206/5.1 |
| 5,690,222 A * | 11/1997 | Peters | 206/339 |
| 5,699,913 A * | 12/1997 | Richardson | 206/470 |

(Continued)

FOREIGN PATENT DOCUMENTS

| | | |
|---|---|---|
| CN | 201064493 | 5/2008 |
| DE | 20-2005016818 | 2/2006 |

(Continued)

*Primary Examiner* — Ernesto Grano

(74) *Attorney, Agent, or Firm* — Fay Kaplun & Marcin, LLP

(57) ABSTRACT

A multi packaging system for packaging of sterile implants includes a carrier plate and a plurality of packings removably attached to the carrier plate. Each of the plurality of packings contains an implant and is individually removable from the carrier plate.

5 Claims, 2 Drawing Sheets

(56) References Cited

U.S. PATENT DOCUMENTS

| | | | |
|---|---|---|---|
| D390,457 S * | 2/1998 | Hoska et al. ................. D9/707 |
| 5,868,244 A | 2/1999 | Ivanov et al. |
| 5,873,860 A | 2/1999 | Kahlert |
| 6,439,390 B1 * | 8/2002 | Kumakura et al. ........... 206/705 |
| 6,726,011 B2 * | 4/2004 | Sarkar et al. ............. 206/362.1 |
| 6,938,770 B2 * | 9/2005 | Nittono et al. .............. 206/485 |
| 7,413,080 B2 * | 8/2008 | Van House .................. 206/470 |
| 7,448,497 B2 * | 11/2008 | Muchin et al. .............. 206/705 |
| 2003/0105552 A1 | 6/2003 | Lunak et al. |
| 2004/0206653 A1 * | 10/2004 | Filion .......................... 206/461 |
| 2008/0200984 A1 * | 8/2008 | Jodaitis et al. ........... 623/17.16 |
| 2008/0302688 A1 | 12/2008 | Iaconi-Forrer et al. |
| 2009/0139893 A1 * | 6/2009 | McGonagle et al. ......... 206/531 |

FOREIGN PATENT DOCUMENTS

| | | |
|---|---|---|
| JP | 2002/153540 | 5/2002 |
| JP | 2007/527762 | 10/2007 |
| JP | 2008-253741 | 10/2008 |
| WO | 2005/092231 | 10/2005 |
| WO | 2006/077432 | 7/2006 |
| WO | 2010/128554 | 11/2010 |

* cited by examiner

MULTI PACKAGING SYSTEM FOR MEDICAL IMPLANTS

PRIORITY CLAIM

The present application claims priority to U.S. Provisional Application Ser. No. 61/367,984 entitled "Multi Packaging System for Medical Implants" filed on Jul. 27, 2010 to Urs Hulliger. The entire contents of this application are incorporated herein by reference thereto.

FIELD OF THE INVENTION

The present invention generally relates to a multi packaging system for packaging of sterile implants comprising a carrier plate with several individual packings which are fixed to the carrier plate as separate units. Therefore, the present invention permits a user to organize the various implants with regard to their places of use and to order the implants with regard to their sizes and product specifications. According to the present invention, the implants may be arranged on a carrier plate, which can be deposited in a box in a manner such that the user can easily find a specific type and size of implant in a short amount of time. Furthermore, the implants are ordered on a short radius in a depositing system whereas otherwise the implants would be deposited in various ways.

BACKGROUND

The storage and accessibility of medical implants (e.g., in an operating room) can help to facilitate the sorting, storing, locating and handling of the implants. Currently, implants are individually deposited in a box positioned on a board in a drawer. To locate a desired implant, the user must read a label on each drawer. This system of depositing may be time-consuming and may require a large area of space.

A multi packaging system is known from the German Utility Patent No. DE 20 2005 016 818 U1. This multi packaging system has the disadvantage that each individual packing is fixed to a separate cardboard stripe by means of a blister and the entirety of individual packings is separately and loosely inserted in a folding pouch.

Another multi packaging system is known from the U.S. Pat. No. 5,249,672. This known multi packaging system has the disadvantage that the objects are not fixed on the (carrier) object but are retained by means of three straight plates. This system would be unsuitable for medical use since objects must be sterilized prior to surgical use. Furthermore, the objects are packaged in a folded cardboard, thus preventing the user from seeing how many objects are available therewithin. Furthermore, this system hinders access to the objects through the opening between the straight plates.

A further multi packaging system is known from the U.S. Pat. No. 5,386,912. This known multi packaging system has the disadvantage that the individual objects are only trapped on the carrier-object but not fixed thereto. In this alternative the complete system is inserted in a folded cardboard, thus having the same disadvantage discussed above with respect to U.S. Pat. No. 5,249,672.

A further multi packaging system is known from the U.S. Pat. No. 4,121,711. This known multi packaging system is also fixed on a folding card, thus also having the same disadvantages discussed above. Specifically, by virtue of the objects being fixed on a folded card, a user is unable to quickly or easily determine how many objects remain on the packaging system.

SUMMARY OF THE INVENTION

The present invention relates to a multi packaging system for packaging of sterile implants comprising a carrier plate and N individual packings, wherein N≥2 and wherein said individual packings are attached to said carrier plate as units whereof each unit can be removed from said carrier plate without being opened.

According to an exemplary embodiment of the present invention, the carrier plate is quadrangular and has four edges, wherein the N individual packing are fixed separately adjacent to one of the edges of the carrier plate. One of the advantages of the multi packaging system according to the present invention is that due to the separate fixation of each individual packing to the carrier plate after removal of one packing the remaining packings are still fixed to the carrier plate and therefore the remaining packings do not drop out from a carrier device.

According to another exemplary embodiment of the present invention, the packings can be removed separately from each other and without being opened by means of a tear-off strip. This allows the remaining packings to remain fixed on the carrier plate although one single packing is removed via the tear-off strip.

According to another exemplary embodiment, the carrier plate is configured like an index card. This configuration allows easier handling and tracking for storage, identification and ordering purposes.

According to another exemplary embodiment said carrier plate comprises continuous numbering with one number located underneath each individual packing on the carrier plate. This configuration allows the user to easily determine how many packings remain on the carrier plate which facilitates the determination of when to order a new multi packaging system.

According to another exemplary embodiment the carrier plate has a legend strip on the top edge. This configuration allows the advantage that each carrier plate can be printed with the object and size or other description of its content. Furthermore, if there are several different carrier plates they can be sorted in series and the user can find the searched carrier plate at one glance.

According to another exemplary embodiment the carrier plate features P≥1 holes through the carrier plate on a free space on the carrier plate which is not covered by the packings. This configuration allows the advantage that the carrier plate can be inserted in a ring binder or something similar.

According to another exemplary embodiment a bar code is printed on the carrier plate, preferably under the second last or last individual packing. This configuration may allow an easy and efficient method of ordering a new carrier plate.

According to another exemplary embodiment the N packings are fixed to said carrier plate at their top edge by means a non-metallic strap and adjacent to one of the edges of said carrier plate in a longitudinal orientation, separate from each other and side by side. This configuration may allow the fixation of all packings on the carrier plate is assured.

According to another exemplary embodiment the N packings are fixed to the carrier plate at their top edges by means of an adhesive, such as glue, and adjacent to one of the edges of the carrier plate in a longitudinal orientation, separate from each other and side by side. This configuration may allow the packings to be fixed separate from each other or together via the adhesive.

According to another exemplary embodiment the N packings are fixed to the carrier plate at their top edges by means of a hot stamping method and adjacent to one of the edges of said carrier plate in a longitudinal orientation, separate from each other and side by side. This configuration allows the advantage that an easy method is provided for fixing plastic packings to a carrier plate which is not made of a metal.

According to another exemplary embodiment said multi packaging system comprises M≥2 carrier plates. This configuration may allow the multi packaging system to be configured as an extensive folder system when there is more than one carrier plate.

According to another exemplary embodiment the carrier plate can be attached via the hole to a mechanical paternoster conveying system. This configuration may allow multiple carrier plates to be inserted in a computer guided mechanical system which can control of the location of each carrier plate. This allows the user to search for a carrier plate and to have the searched carrier plate delivered to a specific location so that the user can easily access the carrier plate and remove a packing from the carrier plate for use.

According to another exemplary embodiment a paternoster conveying system recognizes a carrier plate by a bar code. This configuration may allow the user to enter the number represented by the bar code into the computer in order to search for and acquire a specific carrier plate.

According to another exemplary embodiment said carrier plate has a front side and a rear side and wherein said N individual packings are attached only to said front side and wherein said rear side is preferably used for receiving a bar code or other identification and administration means. This configuration may allow for easy ordering and/or a computerized searching database.

According to another exemplary embodiment said carrier plate has a front side and a rear side and wherein said N individual packings are attached to both of said sides. This configuration may allow a carrier plate to be loaded with twice the number of packings.

BRIEF DESCRIPTION OF THE DRAWINGS

Several exemplary embodiments of the present invention will be described in the following by way of example and with reference to the accompanying drawings in which.

DETAILED DESCRIPTION

The present invention relates to a packaging system for medical implants. The exemplary packaging system provides a plurality of individually packaged implants that are fixed to a carrier plate, the carrier plate being configured to permit a physician or other user to remove individual implants. The carrier plate is also provided with labels indicating a number of remaining implants on the carrier plate, thus providing the physician with a quick reading of the number of implants to facilitate performing of a particular procedure, as those skilled in the art will understand.

Figure 1:
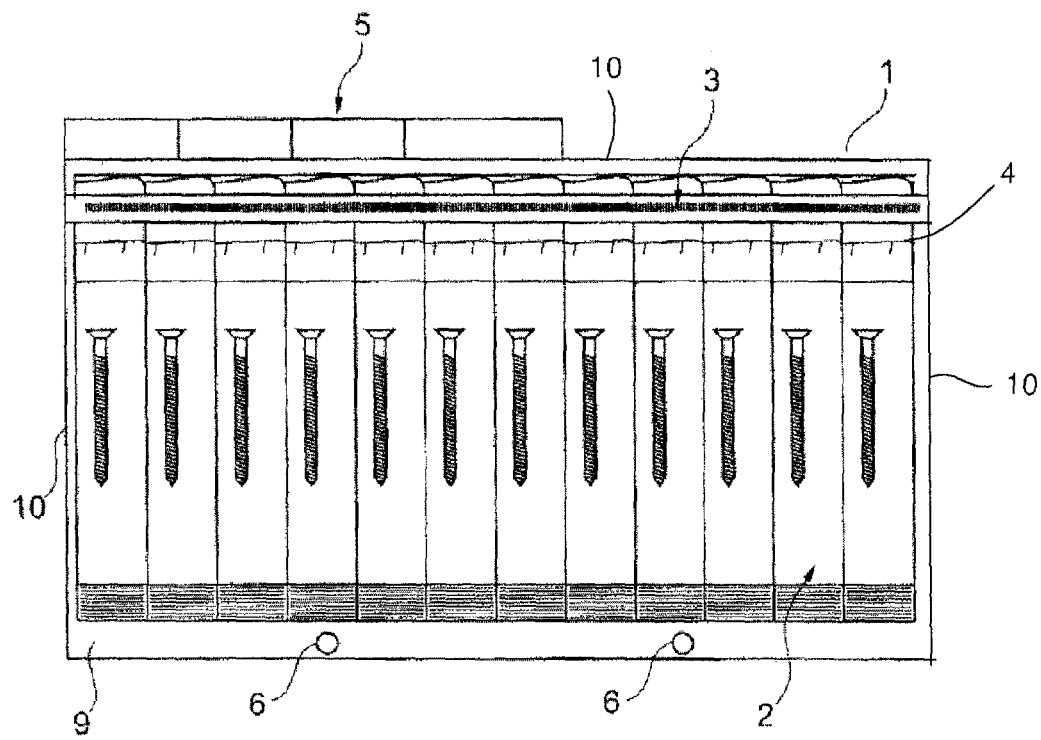
FIG. 1 illustrates a top view of an exemplary embodiment of the multi packaging system according to the present invention.
Figure 2:
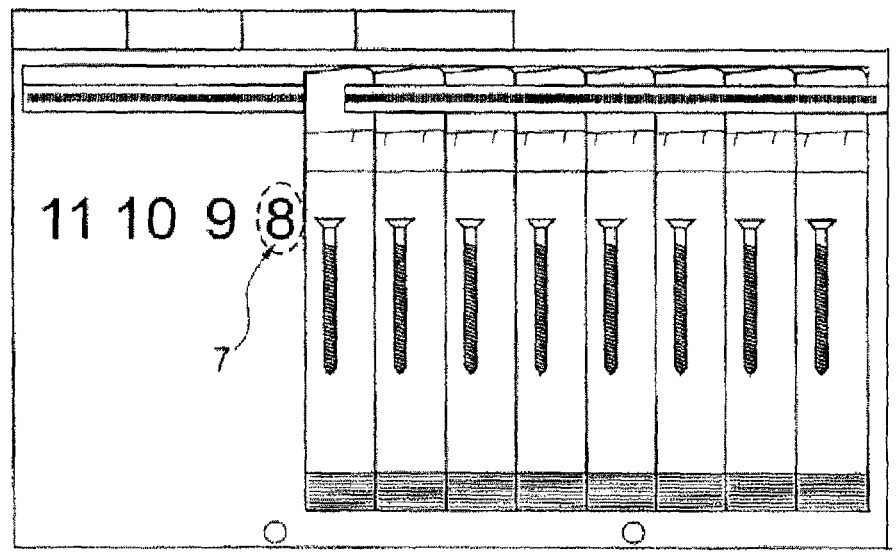
FIG. 2 illustrates a top view on an exemplary embodiment of FIG. 1 of the multi packaging system according to the present invention showing printed numbers underneath each of the individual packings on the carrier plate.
Figure 3:
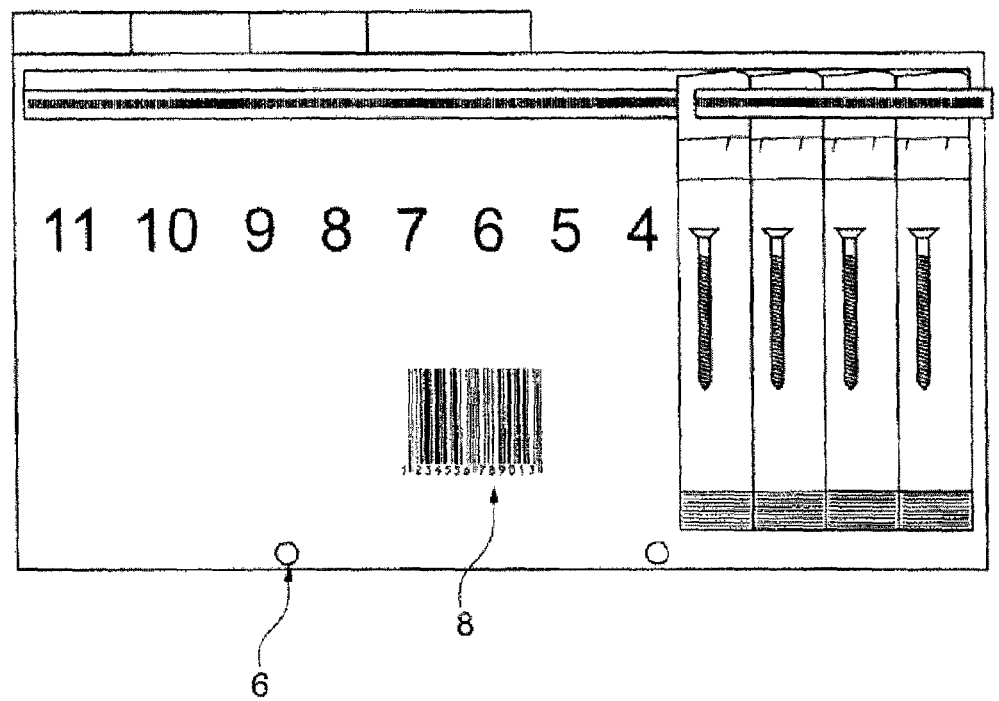
FIG. 3 illustrates a top view on an exemplary embodiment of FIG. 1 of the multi packaging system according to the present invention with a printed bar code.

FIGS. 1-3 illustrate an exemplary embodiment including a multi packaging system 1 comprising N number of sterile individual packings 2 fixed to a carrier plate 9. Each of the individual packings 2 may contain an implant such as, for example, a bone fixation element. The multi packaging system 1 may comprise more than one carrier plate 9 such that each carrier plate 9 holds packings 2 containing implants of a particular type and/or size. For example, a first carrier plate 9 may hold packings 2 containing bone fixation screws that are 40 mm in length while a second carrier plate 9 (not shown) may hold packings 2 containing bone fixation screws that are 42 mm in length. The carrier plate 9 may be quadrangular having four straight edges 10, similar to an index card, for example. The carrier plate 9 may include a legend strip or tab 5 along one edge 10 so that the specific type and/or size of the implant may be indicated thereon. The carrier plate 9 may include at least one hole 6 through a free space of the carrier plate 9, that is not covered by any of the packings 2, for insertion in a ringed binder or other similar device. It will be understood by those of skill in the art that a quadrangular carrier plate 9 permits efficient organization of the packings 2 and ease of storage of the carrier plates 9. It will be understood by those of skill in the art, however, that the carrier plate 9 may be any of a variety of shapes so long as the carrier plate permits individual packings 2 to be affixed thereto.

The individual packings 2 may be fixed to the carrier plate 9 independently of one another via a non-metallic strap 3 adjacent to an edge 10 of the carrier plate 9. The individual packings 2 may be positioned side by side on the carrier plate 9, in a longitudinal orientation such that the non-metallic strap 3 fixes a first end of each of the individual packings 2 to the carrier plate 9. The non-metallic strap 3 may be torn off to permit the packings 2 to be individually removed from the carrier plate 9 and without having to open the individual packings 2. Alternatively, the individual packings 2 may be fixed to the carrier plate 9 via any other known fixation process such as, for example, using an adhesive material (e.g. glue) or a hot stamping method. The packings 2 may include a perforated strip 4 along a portion thereof for opening the packings 2 after the packings 2 have been removed from the carrier plate 9.

The carrier plate 9 may include a continuous numbering 7 printed thereon, underneath the individual packings 2 such that the numbering 7 indicates a number of packings 2 remaining on the carrier plate 9 as each of the packings 2 are removed therefrom. For example, a carrier plate 9 holding twelve packings 2 may be printed with continuous Arabic numerals "11" to "1" from left to right such that the numerals are revealed as each of the packings 2 are removed from the carrier plate 9. As shown in FIG. 2, for example, four packings 2 have been removed thus far, revealing numerals "11" to "8" and indicating that "8" packings remain. The remaining numbers "7" to "1" are printed underneath the remaining individual packings 2 on the carrier plate 9 and are revealed as each additional packing 2 is removed from the carrier plate 9. The continuous numbering 7 shown in FIG. 2 has been printed to facilitate removal of the packings 2 from left to right. It will be understood by those of skill in the art, however, that the continuous numbering 7 may also be printed for removal of the packings 2 from right to left.

As shown in FIG. 3, the carrier plate 9 may also include a barcode 8 printed thereon, the barcode 8 corresponding to the particular type and/or size of the implants held on the carrier plate 9. Thus, when a limited number of packings 2 remain on the carrier plate 9, the barcode 8 may simply be scanned to order additional implants of that particular type and/or size. The barcode 8 may be printed in a desired location on the carrier plate 9 such that visibility of the barcode 8 indicates that it is time to order additional implants. It will be understood by those of skill in the art that the barcode 8 may be used in a variety of different ways to track inventory.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A packaging system for medical implants, comprising:
   a first substantially planar carrier body having a first surface and a second surface;
   a first individually packaged medical implant removably attached to the first surface of the first carrier body in a fixed position relative to the first carrier body; and
   a second individually packaged medical implant removably attached to the first surface of the first carrier body adjacent the first medical implant, wherein the first and second medical implants are configured to prevent the second medical implant from being removed until the first medical implant is removed.

2. The packaging system of claim 1, wherein the first carrier body is provided with labels configured to indicate a remaining number of medical implants as each of the medical implants is removed therefrom.

3. The packaging system of claim 1, further comprising a second carrier body having a third surface and a fourth surface and configured to removably house a third and fourth medical implant thereon, the third and fourth medical implants being different from the first and second medical implants.

4. The packaging system of claim 3, wherein the first and second carrier bodies comprise first and second bores extending therethrough, respectively, to permit attachment thereof to a mechanical paternoster conveying system configured to recognize each of the first and second carrier plates via respective bar codes printed thereon.

5. The packaging system of claim 1, wherein the first and second medical implants are attached to the first carrier body by one of a non-metallic strap, an adhesive material and hot stamping.

* * * * *